United States Patent
Zeide et al.

(10) Patent No.: US 7,491,186 B2
(45) Date of Patent: Feb. 17, 2009

(54) WRIST AND ELBOW BRACE

(76) Inventors: Michael Stuart Zeide, 2306 Embassy Dr., West Palm Beach, FL (US) 33401; Henry Pong, 7531 Colony Plam Dr., Boynton Beach, FL (US) 33436

(*) Notice: Subject to any disclaimer, the term of this patent is extended or adjusted under 35 U.S.C. 154(b) by 134 days.

(21) Appl. No.: 11/449,333

(22) Filed: Jun. 8, 2006

(65) Prior Publication Data
US 2006/0282033 A1    Dec. 14, 2006

Related U.S. Application Data

(60) Provisional application No. 60/690,665, filed on Jun. 14, 2005.

(51) Int. Cl.
*A61F 5/00* (2006.01)
(52) U.S. Cl. ............................. 602/20; 602/5
(58) Field of Classification Search ............ 602/5, 602/20, 21, 22; 482/127; 128/877–879, 128/881
See application file for complete search history.

(56) References Cited

U.S. PATENT DOCUMENTS

| | | |
|---|---|---|
| 2,703,082 A | 3/1955 | Emert |
| 4,048,991 A | 9/1977 | Marx |
| 4,191,373 A | 3/1980 | Lancellotti |
| 4,763,901 A | 8/1988 | Richter |
| 4,899,735 A | 2/1990 | Townsend et al. |
| 4,941,460 A | 7/1990 | Working |
| 4,949,957 A | 8/1990 | Cucchiara |
| D337,180 S | 7/1993 | Bailey |
| 5,662,595 A | 9/1997 | Chesher et al. |
| 5,685,830 A | 11/1997 | Bonutti |
| 5,759,165 A | 6/1998 | Malewicz |
| 5,865,695 A | 2/1999 | Mahala et al. |
| 5,865,714 A | 2/1999 | Marlowe |
| 5,891,079 A | 4/1999 | Barnes |
| 5,954,678 A | 9/1999 | Cruz |
| 6,059,834 A * | 5/2000 | Springs ............... 623/32 |
| 6,117,097 A | 9/2000 | Ruiz |
| 6,179,799 B1 | 1/2001 | Doran |
| 6,790,165 B2 * | 9/2004 | Huang ............... 482/79 |
| 2003/0073941 A1 | 4/2003 | Betz |

(Continued)

*Primary Examiner*—Kim M Lewis
(74) *Attorney, Agent, or Firm*—Darby & DarbyPC; Robert J. Sacco

(57) ABSTRACT

The invention relates to an orthosis (100) and method for the treatment of wrist and elbow illnesses. The orthosis (100) includes a first cuff (101) adapted to be secured to a hand of a user. A second cuff (102) is adapted to be secured to an upper arm portion above an elbow joint of the user. The first cuff (101) and the second cuff (102) include a first attachment point (103) and a second attachment point (104), respectively. The orthosis (100) also includes a resilient member (105) having a first end (106) and a second end (107) opposing the first end (106). The first end (106) of the resilient member (105) is attached to the first attachment point (104) of the first cuff (101). The second end (107) of the resilient member (105) is attached to the second attachment point (104) of the second cuff (102). The first attachment point (103) and the second attachment point (104) are positioned such that a wrist extension force and a forearm extension force are opposed by a counteracting force produced by the resilient member (105). The counteracting force opposes the rotation of the forearm relative to the upper arm about the elbow joint and maintains the wrist in a substantially flexion position.

20 Claims, 3 Drawing Sheets

U.S. PATENT DOCUMENTS

2004/0138597 A1 7/2004 Varn
2004/0152569 A1 8/2004 Lerner
2006/0106328 A1* 5/2006 Sieller et al. ................ 602/21

* cited by examiner

WRIST AND ELBOW BRACE

CROSS REFERENCE TO RELATED APPLICATIONS

This application claims the benefit of priority to U.S. provisional patent application Ser. No. 60/690,665, filed on Jun. 14, 2005, which is incorporated by reference as if fully rewritten herein.

BACKGROUND OF THE INVENTION

1. Statement of the Technical Field

The present invention relates to an orthopedic device. More particularly, the invention relates to an orthosis for the treatment of illnesses of the wrist and elbow.

2. Description of the Related Art

In tendinosis, wear and tear in the wrist and elbow joints is thought to lead to tissue degeneration. Numerous occupational and recreational activities often exacerbate the tendinosis. Such activities include, but are not limited to, typing, grasping a computer mouse, gardening, playing racket sports, and picking up and holding objects. A degenerated tendon, such as the tendons in the wrist and elbow, usually has an abnormal arrangement of collagen fibers. As a result, the body produces an inflammatory response. Special inflammatory cells make their way to the injured tendinous tissues to assist in the healing process.

In wrist injuries, this inflammation is sometimes manifested in or around the carpal and/or ulnar tunnels, compressing the nerves running through these tunnels. When the inflammation is centered around the medial nerve of the wrist, a condition known as carpal tunnel syndrome is produced. When the inflammation is centered around the ulnar nerve, a condition known as ulnar tunnel syndrome is produced. Typical symptoms of carpal and ulnar tunnel syndromes include, but are not limited to, tingling, numbness, night time wakening, pain, coldness, and weakness in parts of the hand.

In elbow injuries, the inflammation is often manifested around the lateral or medial epicondyles of the humeral bone. When the inflammation surrounds the lateral epicondyl, it is commonly referred to as "tennis elbow," or lateral epicondylitis. When the inflammation is centered around the medial epicondyl, it is commonly referred to as "golfer's elbow," or medial epicondylitis.

In the case of lateral or medial epicondylitis, the body produces a type of cells called fibroblasts. When this occurs, the collagen fibers in the elbow tendon lose their strength. These fibers become fragile and can break with too much physical activity, developing small tears in the forearm tendon. Although the body tries to heal these small tears, constant strain and overuse keep re-injuring the tendon. Each time the collagen fibers break down, the body responds by forming scar tissue in the tendon. Eventually, the tendon becomes thickened from extra scar tissue and the healing process loses its effectiveness. The scar tissue never has a chance to fully heal, leaving the injured areas weakened and painful.

In addition to the aforementioned medical conditions, there can also be inflammation of the fluid filled tissue sheath (called synovium) that surrounds the tendons of the wrist and/or elbow. This inflammatory condition is commonly called tenosynovitis of the wrist and/or elbow. When the wrist and/or elbow tendons are inflamed, the synovium swells. As a result, the tendons cannot slide easily through the synovium, causing swelling and pain at the wrist and/or elbow joints.

Another medical condition, known as mogigraphia or "writer's cramp," refers to a disorder of the hand due to excessive fine motor activity. Writer's cramp is thought to result from a problem of motor control involving the basal ganglia of the brain. Common manifestations of simple writer's cramp include excessive gripping of the pen, flexion, and sometimes deviation of the wrist, elevation of the elbow, and occasional extension of a finger or fingers causing the pen to fall from the hand. Sometimes the disorder progresses to include the elevation of shoulders or the retraction of the arm while writing.

In the field of orthopedics, there are numerous treatment options for treating writer's cramp, tendinosis and related illnesses of the wrist and elbow. Over the years, some of the treatment devices and methods in this particular area have been the use of supports, wraps, armbands with or without air bubbles, static splinting and casting with fiberglass or plaster materials, as well as magnets, ultrasound, acupuncture, physical therapy, cortisone patches and/or injections, ice/heat packs, and anti-inflammatory medications.

Various other treatment methods attempt to treat the condition by immobilizing the muscle(s), tendons, ligaments, and/or capsular structures to prevent their use. This idea of immobilization is based upon an agonist-antagonist functional interaction in every activity of the elbow, forearm, wrist, hand and fingers. The rationale for immobilization is to relax the muscle to allow it to heal. Relaxing the muscle in this way can ameliorate, modify, and reduce inflammation.

There have been many attempts in the art to design an orthosis for the elbow joint to treat tendinosis and related illnesses of the wrist and elbow. For example, U.S. Pat. No. 5,662,595 to Chesher et al. provides a supination-pronation orthosis for the elbow joint. The orthosis includes a hand and wrist cuff that restricts wrist flexion, essentially immobilizing the wrist joint. A flexible torsion unit is mounted to extend between the upper arm cuff and the hand and wrist cuff along the forearm of the patient. The torsion unit selectively opposes rotation of the forearm of the patient about the elbow joint.

U.S. Pat. No. 4,899,735 to Townsend et al. discloses a torsion bar splint for a patient's forearm. The device retains and restricts the forearm in the position to which it is rotated.

U.S. Patent Application Pub. No. US2004/0138597 to Varn teaches a dorsal blocking hand orthosis. The orthosis has a rigid hand splint member which has a forearm portion attached to a finger portion, which are adapted to receive a patient's hand so that a forearm portion and a splint member rest on the dorsal portion of the patient's wrist and forearm.

However, one drawback to the devices shown in the art is that restricting a muscle's use by permanent joint immobilization can cause joint stiffness. Some other major problems associated with permanently immobilizing the elbow joint and/or wrist joint include joint stiffness, contractures, muscle atrophy, skin irritation, and functional restrictions.

It is also known in the medical and scientific literature, and specifically in the field of hand surgery, that tendons can be repaired and sewn together. Typical methods used in treating a post-operative patient are to allow the repaired tendons to heal by an external fixation device that immobilizes movement at the elbow joint. As discussed, such a device can cause stiffness (contractures, muscle atrophy, skin irritation, and functional restrictions) in the neighboring joints.

Therefore, what is needed in the art is an orthosis that can restrict the contraction of muscles connected to tendons attached at either the lateral or medial epicondyles. At the same time, the orthosis should not immobilize movement at the wrist and elbow joints. Thus, the orthosis should allow the muscle(s) tendons, ligaments, and/or capsular structures in question to relax to prevent aggravating the tendinosis and its related illnesses of the wrist and elbow.

SUMMARY OF THE INVENTION

The invention is an orthosis for the treatment of illnesses of the wrist and elbow. The orthosis includes a first cuff adapted to be secured to a hand of a person. A second cuff is adapted to be secured to an upper arm portion above an elbow joint of the person. The second cuff includes a slip-resistant layer that is disposed on the upper arm portion of the person. First and second attachment points are disposed on the first and second cuffs, respectively. In one embodiment of the invention, the second attachment point is a swivel loop fastener.

The orthosis includes a resilient member having a first end and a second end opposing the first end. The first and second ends are attached to the first and second attachment points, respectively. The first and the second attachment points are positioned such that a wrist extension force and a forearm extension force are opposed by a counteracting force produced by the resilient member. The counteracting force produced by the resilient member opposes the rotation of the forearm relative to the upper arm about the elbow joint and maintains the wrist in a substantially flexion position. The resilient member is a member of the group consisting of a shock cord, rubber band, and elastomer. Furthermore, the counteracting force of the resilient member is selectively variable. According to one embodiment of the invention, the counteracting force is selectively variable between 0 and 5 pounds.

In one embodiment of the invention, the orthosis maintains the wrist in a generally dorsiflexion position. The dorsiflexion position restricts the contraction of one or more muscles connected to a lateral epicondyle. According to another embodiment of the invention, the orthosis maintains the wrist in a generally palmarflexion position. The palmarflexion position restricts the contraction of one or more muscles connected to a medial epicondyle.

The orthosis is designed such that the first cuff is adjusted to the size of a person's hand. The second cuff is adjusted to the size of the person's upper arm. In one embodiment of the invention, hook and pile fasteners can be used to secure the first cuff to the hand of a person and to secure the second cuff to the upper arm of the person.

In another aspect of the invention, the invention relates to a method for treating illnesses of the wrist and elbow. The method includes adapting a first and second cuff to be secured to a hand and upper arm of a person, respectively. A first and second attachment point is disposed on the first and second cuffs, respectively. The method includes the step of attaching a resilient member having a first end and a second end opposing the first end to the first and second attachment points, respectively. The first and second attachment points are positioned such that the extension and rotation of the forearm relative to the upper arm about the elbow joint is opposed by a counteracting force produced by the resilient member. The first and second attachment points are positioned such that the extension and rotation of the hand relative to the forearm about the wrist joint is opposed by the counteracting force produced by the resilient member, maintaining the wrist in a substantially flexion position.

DETAILED DESCRIPTION OF THE PREFERRED EMBODIMENTS

Figure 1:
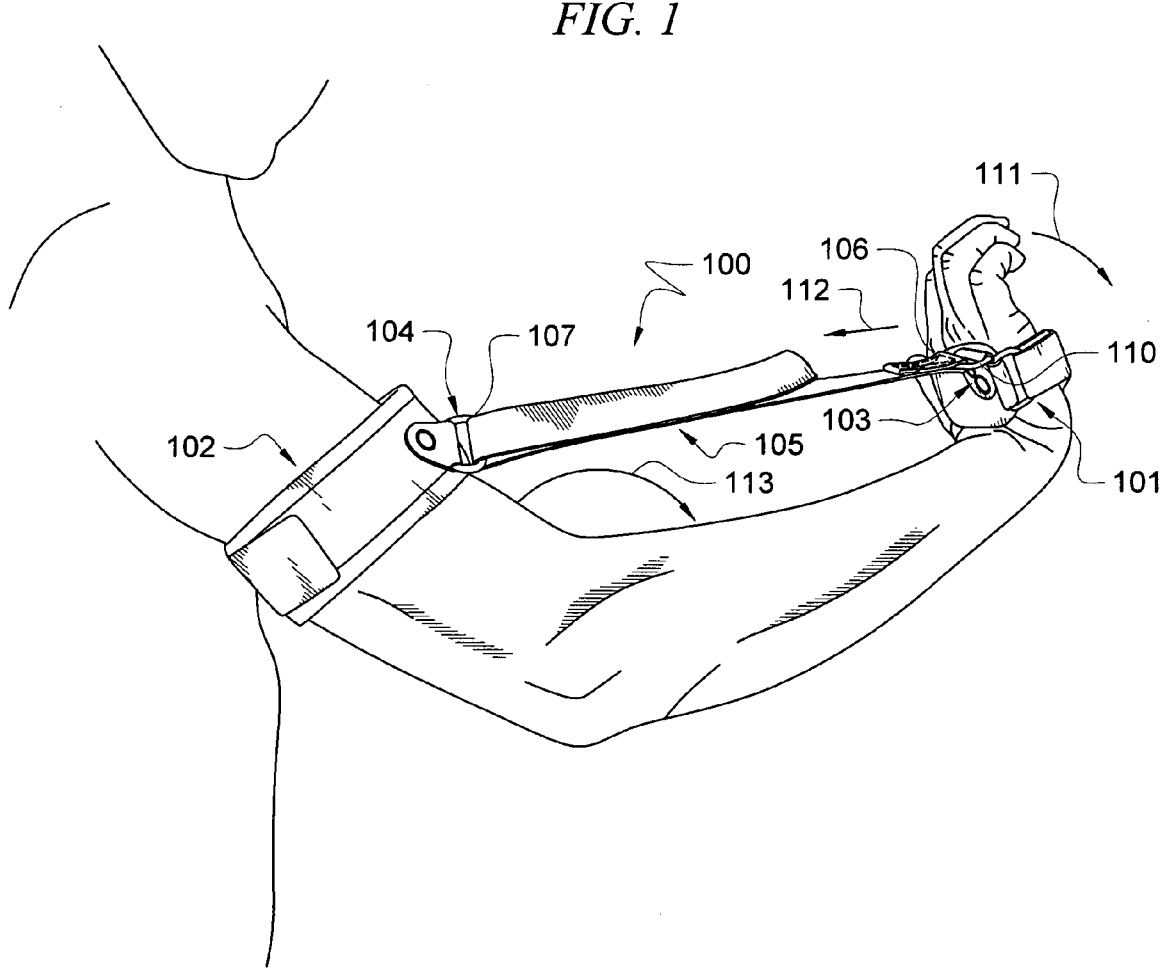
FIG. 1 is a perspective view of an orthosis in its intended use for the treatment of lateral epicondylitis that is useful for understanding the invention.
Figure 2:
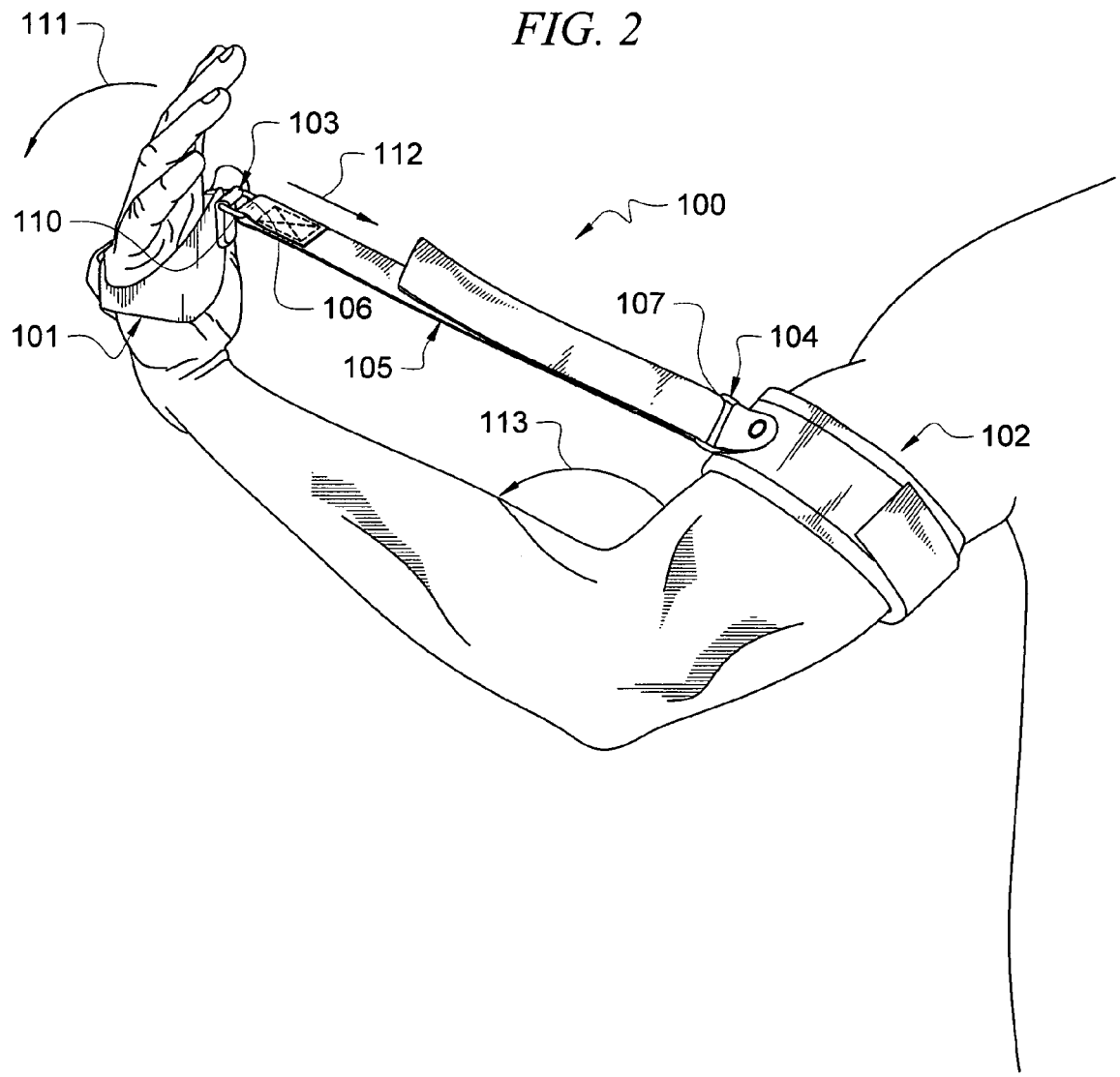
FIG. 2 is a another perspective view of the orthosis of FIG. 1 in its intended use for the treatment of medial epicondylitis that is useful for understanding the invention.

Referring to FIGS. 1 and 2, shown are perspective views of the preferred embodiment of an orthosis 100, each figure illustrating a different intended use for the treatment of epicondylitis. FIG. 1 illustrates the use of the orthosis for the treatment of lateral epicondylitis. FIG. 2 illustrates the use of the orthosis for the treatment of medial epicondylitis.

The orthosis 100 can comprise a first cuff 101 that is positioned about the hand of a user. A second cuff 102 can be disposed about the user's upper arm, namely the humeral portion of the arm above the elbow. A first attachment point 103 can be disposed on the first cuff 101. A second attachment point 104 can be disposed on the second cuff 102. A resilient member 105, having a first end 106 and a second end 107 opposing the first end 106, can be attached to the first attachment point 103 and second attachment point 104, respectively.

Referring specifically to FIG. 1, the orthosis 100 is worn such that the wrist and hand are reverted and maintained in a generally dorsiflexion position, whereby the back of the hand is positioned towards the forearm. By maintaining the wrist and hand in a dorsiflexion position, the orthosis 100 restricts the contraction of one or more muscles connected to the lateral epicondyle. The muscles restricted include, but are not limited to, extensor carpi radialis longus, extensor carpi radialis brevis, extensor carpi ulnaris, anconeus, extensor digiti minimi, extensor digitorum, and supinator muscles. As a result, the degree of muscle tension in the region of muscular attachment to the lateral epicondyle is reduced.

Referring specifically to FIG. 2, the orthosis 100 is worn such that the wrist and hand are reverted and maintained in a generally palmarflexion position, whereby the palm of the hand is positioned towards the forearm. By maintaining the wrist and hand in a palmarflexion position, the orthosis 100 restricts the contraction of one or more muscles connected to the medial epicondyle. The muscles restricted by this user position for the treatment of medial epicondylitis include, but are not limited to, flexor carpi radialis, flexor carpi ulnaris, palmaris longus, flexor digitorum superficialis, and pronator teres muscles. As a result, the degree of muscle tension in the region of muscular attachment to the medial epicondyle is reduced.

In addition to resting the affected muscles, both user positions advantageously allow the tendons, ligaments, and/or capsular structures to rest. Such rest will allow these structures to heal more effectively. Consequently, inflammation will be prevented, modified, and reduced in a desirable manner.

Figure 3:
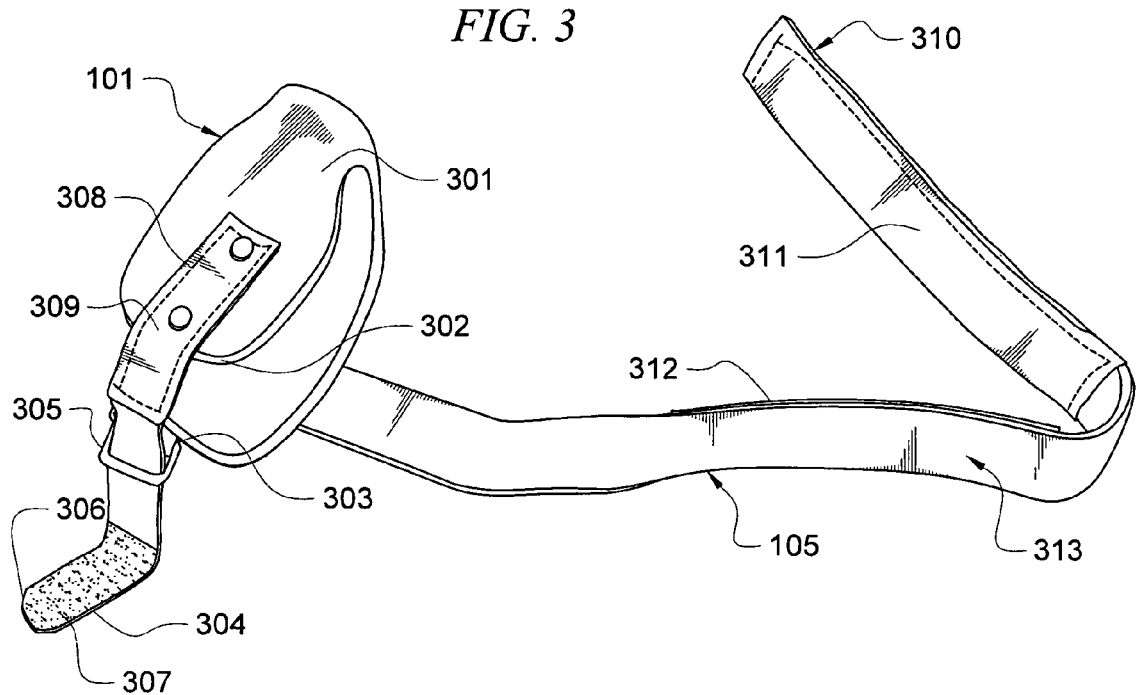
FIG. 3 is a perspective view of a first cuff and resilient member for the orthosis of FIGS. 1 and 2 that is useful for understanding the invention.

Referring to FIG. 3, shown is the first cuff 101 which can be formed of any of numerous materials suitable for comfortable wear. In one embodiment of the invention, the first cuff 101 can be formed from modified polyethylene and formed into a U-shaped plastic element 301. In other embodiments of the invention, the first cuff 101 can be formed from fabric webbing, cloth, other plastics, composite, or other type of material. The U-shaped plastic element 301 can include ends 302, 303 that are adjustably biased towards each other using a hand strap 304 and hand loop 305. A distal end portion 306 of the hand strap 304 can include a portion of a loop fastener 307. A proximal end portion 308 of the hand strap 304 can include a pile fastener 309. The hand strap 304 is threaded through the hand loop 305. The distal end portion 306 and the proximal end portion 308 are secured by the portion of the loop fastener 307 and pile fastener 309. The U-shaped plastic element 301 can be further shaped to conform to the palm of the user, as well as the natural curvature of the back of the hand. It should be understood that the invention is not limited to any particular embodiment of cuff shape. Any shape that can fit comfortably around the palm of a user's hand can be used. According to another embodiment of the invention, the first cuff 101 can be formed as a loop of fabric material that can be fitted about the palm area of the hand and extends about the back area of the hand.

Figure 4:
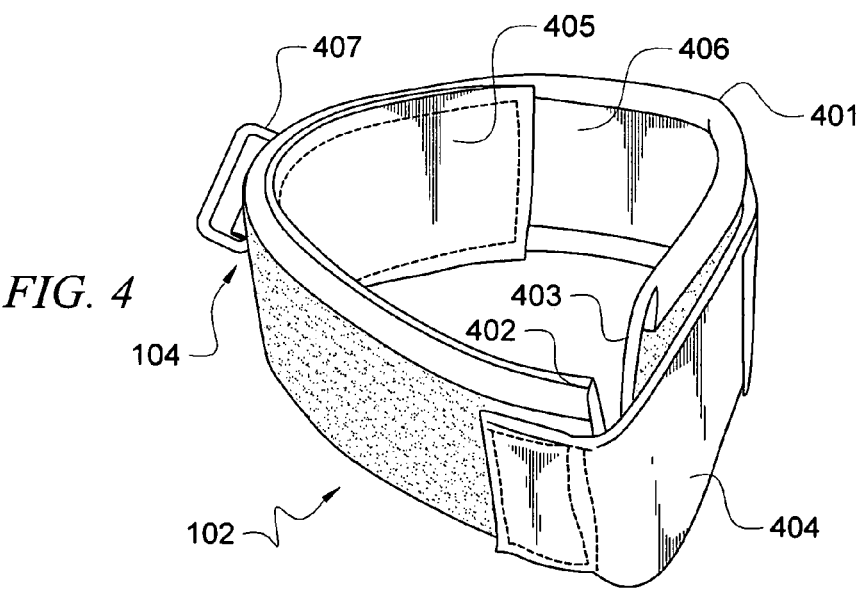
FIG. 4 is a perspective view of a second cuff for the orthosis of FIGS. 1 and 2 that is useful for understanding the invention.

Referring now to FIG. 4, a perspective view of the second cuff 102 is shown. The second cuff 102 is designed to be disposed around the upper arm portion of the user/patient. The second cuff 102 can be formed of any one of the various types of materials that can be used for the first cuff 101. The second cuff 102 can be composed of a fabric strap 401 with strap ends 402, 403 that can be clamped together by an adjustable strap portion 404. The adjustable strap portion 404 can be secured to the fabric strap 401 with a 'loop and pile', snap-on, or magnetic fastener. According to another embodiment of the invention, the adjustable strap portion 404 can be threaded through a second cuff loop (not shown) to facilitate loosening or cinching of the second cuff 102. The shape of the second cuff 102 can be formed as a loop of material or in any other configuration suitable for attachment to a user's arm. In another embodiment of the invention, an elastic clamp or clip (not shown) can also be used for this purpose. The second cuff 102 can also include a slip-resistant layer 405 disposed on an inner surface 406 that grasps the upper arm portion of the user/patient.

The second cuff 102 can also include a second attachment point 104 having a swivel loop fastener 407 disposed thereon. According to the embodiment of the orthosis 100 shown in FIGS. 1 and 2, a second end 107 of the resilient member 105 can removably attach to the second attachment point 104 by a loop and pile fastener 311, 312 disposed on the resilient member 105. According to FIGS. 3 and 4, the resilient member 105 can be a resilient strap that is threaded through the swivel loop fastener 407. A distal portion 310 of the resilient member 105 that is threaded through the swivel loop fastener 407 contains loop material 311. When the resilient member 105 is folded back, the loop material 311 attaches to pile material 312 disposed on a medial portion 313 of the resilient member 105. The slip-resistant layer 405 and swivel loop fastener 407 can assist in maintaining a suitable position for the treated arm.

Referring back to FIGS. 1-2, a fixed loop 110 can be disposed at the first attachment point 103. The particular positioning of the first attachment point 103 is not critical to the invention. Rather, the actual position of the first attachment point 103 can vary depending upon the particular medical condition and comfort level of the user/patient. The fixed loop 110 at the first attachment point 103 can be fixedly connected to the first end 106 of the resilient member 105. However, it should be noted that the first end 106 of the resilient member 105 can be removably connected to the fixed loop 110.

The first and second attachment points 103, 104 can serve as anchors for first and second ends 106, 107 of the resilient member 105. When the orthosis is worn by the user/patient, a wrist extension force produced by the natural positioning of the wrist joint tends to bias the user's hand in a direction 111 that increases the angle formed between the hand and the forearm. This wrist extension force can produce a counteracting force by the resilient member 105. The counteracting force acts in a direction 112 from the first attachment point 103 to the second attachment point 104. The counteracting force is responsible for maintaining the wrist in a substantially flexion position, as shown in FIGS. 1 and 2.

In addition to the wrist extension force, a forearm extension force moving in the direction 113 can also be produced as a result of arm muscle contraction. To counter this forearm extension force, the counteracting force can also oppose the rotation of the forearm relative to the upper arm about the elbow joint.

The resilient member 105 can be comprised of one or more elastic elements formed from a spring or elastic band. The resilient member 105 can be advantageously aligned with the affected muscle(s), tendons, ligaments, and/or capsular structures of the user's arm. According to the embodiment of the invention shown in FIGS. 1-3, the counteracting tension force of the band can be adjusted by loosening or tightening the resilient member 105 by readjusting the attachment location of the loop and pile fastener 311, 312. It should be noted that the invention is not limited in this regard and other embodiments of the means of adjusting the counteracting force can be used. For example, a ratchet or turnbuckle adjustment mechanism can also be used (not shown). Moreover, the counteracting force can be adjusted to a value approximately between 0 and 5 pounds. However, the invention is not limited in this regard and any number of ranges may be selected, so long as a suitable counteracting force can maintain the wrist and hand in a substantially flexion position. The resilient member 105 can be advantageously selected to have an elasticity that allows the user/patient to function while the orthosis 100 is worn. Consequently, the user/patient is able to flex his/her wrist against the opposing force created by the resilient member 105 to utilize his/her wrist and hand in an almost normal function.

As mentioned above, the orthosis 100 can be worn in two different user positions depending on the particular type of epicondylitis to be treated. If the orthosis 100 is worn such that the resilient member 105 is worn along the lateral side of the forearm, then the orthosis 100 is used for the treatment of lateral epicondylitis, as shown in FIG. 1. When the orthosis 100 is worn such that the resilient member 105 is worn along the medial side of the forearm, as shown in FIG. 2, the orthosis 100 is used for the treatment of medial epicondylitis.

While specific embodiments of the invention have been disclosed, it will be appreciated by those skilled in the art that various modifications and alterations to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. An orthosis, comprising:
   a first cuff comprising a shaped plastic element having a size and a contour that conforms to a palm of a person's hand during use of said orthosis, and to a natural curvature of a dorsum of said person's hand during use of said orthosis;
   a means adapted for securing said first cuff on said person's hand;
   a second cuff adapted to be secured to an upper arm portion above an elbow joint of a person;

a first attachment point configured to be disposed at a location on said first cuff adjacent to said palm or said dorsum of said person's hand during use of said orthosis, said location offset from a medial line of said palm defined by a third metacarpal bone of said person's hand during use of said orthosis;

a second attachment point disposed on said second cuff; and a resilient member having a first end and a second end opposing said first end, said first and second ends attached to said first and second attachment points respectively;

wherein said first and second attachment points are positioned such that a wrist extension force produces a counteracting force by said resilient member, maintaining said wrist in a substantially flexion position.

2. The orthosis as recited in claim 1, wherein said wrist is maintained in a generally dorsiflexion position.

3. The orthosis as recited in claim 2, wherein said dorsiflexion position restricts a contraction of at least one muscle connected to a lateral epicondyle.

4. The orthosis as recited in claim 1, wherein said wrist is maintained in a generally palmarflexion position.

5. The orthosis as recited in claim 4, wherein said palmarflexion position restricts a contraction of at least one muscle connected to a medial epicondyle.

6. The orthosis as recited in claim 1, wherein at least one of said first and second cuffs is adjustable.

7. The orthosis as recited in claim 6, wherein said first cuff is adapted to be secured to said hand and said second cuff is adapted to be secured to said upper arm by loop and pile fasteners.

8. The orthosis as recited in claim 1, wherein said resilient member is a member of the group consisting of a shock cord, rubber band, and elastomer.

9. The orthosis as recited in claim 8, wherein the counteracting force by said resilient member is adjustably varied.

10. The orthosis as recited in claim 9, wherein the counteracting force varies approximately between 0 and 5 pounds.

11. The orthosis as recited in claim 1, wherein said second attachment point is defined as a swivel loop fastener.

12. The orthosis as recited in claim 1, wherein said second cuff includes a slip-resistant layer that grasps said upper arm portion.

13. An orthosis, comprising:

a first cuff comprising a shaped plastic element having a size and a contour that conforms to a palm of a person's hand during use of said orthosis, and to a natural curvature of a dorsum of said person's hand during use of said orthosis;

a means adapted for securing said first cuff on said person's hand;

a second cuff adapted to be secured to an upper arm portion above the elbow joint of a person;

a first attachment point configured to be disposed at a location on said first cuff adjacent to said palm or said dorsum of said person's hand during use of said orthosis, said location offset from a medial line of said palm defined by a third metacarpal bone of said person's hand during use of said orthosis;

a second attachment point disposed on said second cuff; and a resilient member having a first end and a second end opposing said first end, said first and second ends attached to said first and second attachment points respectively;

wherein said first and second attachment points are positioned such that a wrist extension force and a forearm extension force are opposed by a counteracting force produced by said resilient member opposing the rotation of the forearm relative to the upper arm about the elbow joint and maintaining said wrist in a substantially flexion position.

14. The orthosis as recited in claim 13, wherein said wrist is maintained in a substantially dorsiflexion position.

15. The orthosis as recited in claim 13, wherein said wrist is maintained in a substantially palmarflexion position.

16. The orthosis as recited in claim 14, wherein said dorsiflexion position restricts a contraction of at least one muscle connected to a lateral epicondyle.

17. The orthosis as recited in claim 15, wherein said palmarflexion position restricts a contraction of at least one muscle connected to a medial epicondyle.

18. The orthosis as recited in claim 13, wherein at least one of said first and second cuffs is adjustable.

19. The orthosis as recited in claim 13, wherein the counteracting force by said resilient member is adjustably varied.

20. A method for treating wrist and elbow illnesses, comprising the steps of:

providing a first cuff adapted to be secured to a hand of a person, said first cuff comprising a shaped plastic element having a size and contour that conforms to a palm of a person's hand, and to a natural curvature of a dorsum of said person's hand;

securing said first cuff to said hand of said person;

securing a second cuff to an upper arm portion above the elbow joint of said person;

disposing a first attachment point at a location on said first cuff adjacent to said palm or said dorsum of said person's hand, said location offset from a medial line of said palm defined by a third metacarpal bone of said person's hand;

disposing a second attachment point on said second cuff;

attaching a resilient member having a first end to said first attachment point and a second end opposing said first end to said second attachment point; and positioning said first and second attachment points such that a wrist extension force and a forearm extension force are opposed by a counteracting force produced by said resilient member for opposing the rotation of the forearm relative to the upper arm about the elbow joint and maintaining said wrist in a substantially flexion position.

* * * * *